United States Patent [19]

Simoens

[11] Patent Number: Plant 6,460

[45] Date of Patent: Dec. 13, 1988

[54] *FICUS BENJAMINA* PLANT NAMED GOLDEN KING

[75] Inventor: Adrien Simoens, Merelbeke, Belgium

[73] Assignee: Golden King Holdings, Inc., Miami, Fla.

[21] Appl. No.: 901,009

[22] Filed: Aug. 27, 1986

[51] Int. Cl.[4] ..... A01H 5/00

[52] U.S. Cl. ..... Plt./88

[58] Field of Search ..... Plt./88

[56] References Cited

PUBLICATIONS

Exotica 4, Graf, Roehrs Co. Publ., 1982, pp. 1563 and 2291.

*Primary Examiner*—Robert E. Bagwill

*Attorney, Agent, or Firm*—Schwartz, Jeffery, Schwaab, Mack, Blumenthal & Evans

[57] ABSTRACT

A *Ficus benjamina* plant named Golden King having a vigorous growth habit, luxuriant green leaves variegated light yellow entirely around the border and irregularly inwardly of the borders, and having good temperature tolerance.

2 Drawing Sheets

The present invention comprises a new and distinct cultivar of *Ficus benjamina,* known by the cultivar name Golden King.

Golden King is the result of an irradiation program carried out under the direction of applicant in Melle, Belgium in 1979. The parent cultivar was an unnamed and unpatented cultivar of *Ficus benjamina* having solid green leaves. The new cultivar was immediately recognizable by its luxuriant green leaves and pleasantly contrasting light yellow variegation in the borders of the leaves and extending inwardly from the border in irregular patterns and amounts. This variegation color characteristic did not previously exist in *Ficus benjamina* cultivars to the best knowledge of applicant.

The first act of asexual reproduction of Golden King was accomplished when stem cuttings were taken in January 1980 in a controlled environment in Melle, Belgium under the supervision of applicant. Horticultural examination of Golden King has demonstrated that the combination of characteristics as herein disclosed for the new cultivar are firmly fixed and are retained through successive generations of asexual reproduction.

Golden King has not been observed under all possible environmental conditions. The phenotype may vary significantly with variations in environment such as temperature, light intensity, and day length. The following observations, measurements and comparisons describe plants grown in Melle, Belgium under greenhouse conditions which approximate those generally used in commercial practice.

The following traits have been repeatedly observed and are determined to be basic characteristics of Golden King which in combination distinguish this *Ficus benjamina* as a new and distinct cultivar:

1. Luxuriant, glossy leaves which are medium green in color and slightly undulating.

2. A light yellow border around the entire leaf. This provides a unique color contrast with the glossy green leaves.

3. The leaves are variegated in irregular patterns inwardly of the borders. To date, all leaves are variegated, with the amount and depth of variegation varying from leaf to leaf. Collectively, the leaves due to the variegation present a pleasant mixture of light yellow and green color, as opposed to the solid green of most cultivars of this species.

4. Golden King is highly resistant to temperature fluctuations. It can be grown at temperatures ranging from 10°–35° C., depending on humidity, soil, light and other growing conditions. To the best knowledge of applicant, Golden King is the most temperature tolerant of the variegated *Ficus benjamina* cultivars presently available. This temperature tolerance extends to shipping, a commercially significant characteristic.

5. A strong plant with vigorous growth habit and superior branching.

6. Relatively close internodes result in a high leaf density, with fifteen (15) or more leaves frequently appearing on a single stem.

In comparison to known cultivars, Golden King is distinguished from its parent by its variegation and its superior temperature tolerance. The growth habit and leaf size and shape are similar to the parent. In comparison to Golden Princess, also an irradiated sport obtained in Melle, Belgium, the variegated border and inner regions are a much lighter color than in Golden Princess, and the border color is continuous and uniform. In Golden Princess, the border variegation is frequently discontinuous.

The accompanying photograhic drawings show a typical mature plant and foliage characteristics of Golden King, with colors being as nearly true as possible with illustrations of this type.

Sheet 1 is a front view of the plant, and Sheet 2 is an enlarged bottom plan view of the bottom of a single leaf of Golden King. Sheet 2 accurately depicts the variegation color, but the main green background color is much darker than the actual color. The main background color is accurately depicted in the photographic comprising Sheet 1 and is accurately set forth in the color value noted below.

In the following description color references are made to The Royal Horticultural Society Colour Chart. The color values were determined in early April in Alexandria, Va. under natural light conditions.

Classification:

*Botanical.*—*Ficus benjamina* c.v. Golden King.

Parentage: Sport obtained in Melle, Belgium by gamma radiation of *Ficus benjamina* cultivar having solid green leaves.

Propagation: By micro stem cuttings.

Plant: Very vigorous grower, producing dense foliage; internode spacing 1.5–3.5 cm., producing fifteen (15) or more leaves per stem.

Leaves:

*Size.*—6–9 cm. in length and 3–4.5 cm. in width at widest area.

*Shape.*—Oval to ovate, acuminate tip extending downwardly; base acute.

*Texture.*—Very glossy.

*Aspect.*—Slightly undulating.

*Margin.*—Smooth.

*Veination.*—Very prominent midrib, veins extending from midrib to margin.

*Color.*—Main color upper surface 137B-C, with borders between 11C and 11D, and irregular variegation extending inwardly from borders also between 11C and 11D; underside slightly lighter; variegation extends through thickness of leaf.

I claim:

1. A new and distinct cultivar of *Ficus benjamina* named Golden King, as illustrated and described, and particularly characterized by its vigorous growth habit, luxuriant green leaves variegated light yellow entirely around the border and irregularly inwardly of the borders, and by its temperature tolerance.

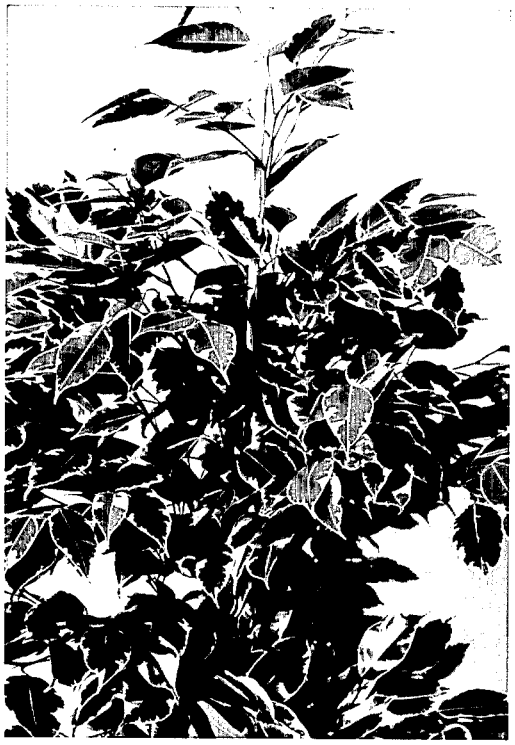

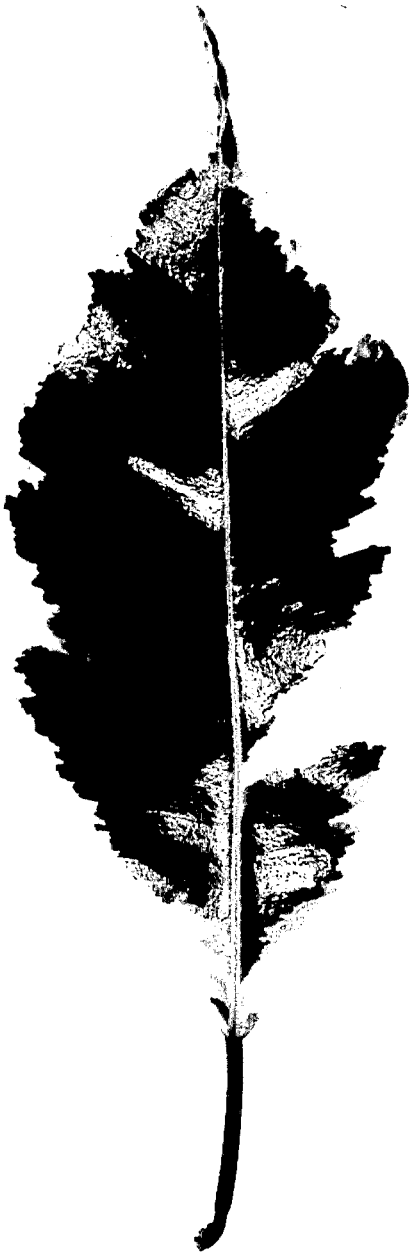

* * * * *